United States Patent
Diana

(10) Patent No.: US 7,368,127 B2
(45) Date of Patent: *May 6, 2008

(54) BIOMEDICAL DEVICES WITH PEPTIDE CONTAINING COATINGS

(75) Inventor: Zanini Diana, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 798 days.

This patent is subject to a terminal disclaimer.

(21) Appl. No.: 10/324,461

(22) Filed: Dec. 19, 2002

(65) Prior Publication Data

US 2004/0121939 A1 Jun. 24, 2004

(51) Int. Cl.
| | |
|---|---|
| G02C 7/04 | (2006.01) |
| A61K 9/00 | (2006.01) |
| A61K 38/02 | (2006.01) |
| A61K 38/16 | (2006.01) |
| A61L 28/00 | (2006.01) |
| A61L 31/00 | (2006.01) |
| A61F 2/00 | (2006.01) |
| A61F 2/01 | (2006.01) |
| A61F 2/02 | (2006.01) |
| A61F 13/00 | (2006.01) |
| C07K 2/00 | (2006.01) |
| C07K 14/00 | (2006.01) |
| C07K 7/08 | (2006.01) |

(52) U.S. Cl. ............ 424/429; 424/400; 424/422; 424/423; 424/427; 424/430; 424/445; 424/447; 530/300; 530/324; 530/326; 530/327; 514/2; 514/12; 514/13; 514/14

(58) Field of Classification Search ............ None
See application file for complete search history.

(56) References Cited

U.S. PATENT DOCUMENTS

| | | |
|---|---|---|
| 3,408,429 A | 10/1968 | Wichterle |
| 3,660,545 A | 5/1972 | Wichterle |
| 4,113,224 A | 9/1978 | Clark et al. |
| 4,197,266 A | 4/1980 | Clark et al. |
| 4,495,313 A | 1/1985 | Larsen |
| 4,680,336 A | 7/1987 | Larsen |
| 4,711,943 A | 12/1987 | Harvey, III |
| 4,833,200 A | 5/1989 | Noishiki et al. |
| 4,889,664 A | 12/1989 | Kindt-Larsen |
| 4,910,277 A | 3/1990 | Bambury et al. |
| 5,034,461 A | 7/1991 | Lai et al. |
| 5,039,459 A | 8/1991 | Kindt-Larsen |
| 5,070,166 A | 12/1991 | Su et al. |
| 5,070,215 A | 12/1991 | Bambury et al. |
| 6,121,027 A | 9/2000 | Clapper et al. |

FOREIGN PATENT DOCUMENTS

| | | |
|---|---|---|
| EP | 164889 A2 | 12/1985 |
| EP | 430517 B1 | 6/1991 |
| EP | 455585 B1 | 11/1994 |
| EP | 0990 924 A1 | 4/2000 |
| WO | WO 96/25183 A2 | 8/1996 |
| WO | WO 01/56627 A1 | 8/2001 |
| WO | WO 02/064183 A1 | 8/2002 |

OTHER PUBLICATIONS

PCT International Search Report, dated Sep. 15, 2004, for PCT Int'l Appln. No. PCT/US03/40654.
Teichman J.M H et al.—Protamine Sulfate and Vancomycin Are Synergistic Against Staphylococcus Epidermidis Prosthesis Infection In Vivo, Jul. 1994, Journal of Urology, Baltimore, MD, pp. 213-216.

*Primary Examiner*—Andrew D. Kosar

(57) ABSTRACT

Biomedical devices with stable peptide coatings are provided. The coatings are formed by incorporating at least one latent reactive component into the reactive mixture, forming a medical device from said reactive mixture and reacting said medical device with a coating effective amount of a coating peptide to bond said coating to the surface by ester or amide linkages.

30 Claims, No Drawings

BIOMEDICAL DEVICES WITH PEPTIDE CONTAINING COATINGS

FIELD OF THE INVENTION

This invention relates to medical devices coated with peptides and a method for coating medical devices with peptides. In particular, the invention provides medical devices on the surfaces of which stable antimicrobial peptide coatings are formed via reaction of nucleophilic moieties of said antimicrobial peptides with latent carboxylic acid groups present in the medical device surface thereby forming ester and/or amide linkages.

REFERENCE TO A SEQUENCE LISTING

A sequence listing is attached hereto and incorporated by reference, in its entirety.

BACKGROUND OF THE INVENTION

Devices for use in and on the human body are well known. The chemical composition of the surfaces of such devices plays a pivotal role in dictating the overall efficacy of the devices. Coatings have been used to enhance desirable properties in these devices. In one example, many devices, including catheters, stents, lenses, and implants require biologically non-fouling surfaces, meaning that bacteria, proteins, lipids, and cells will not adhere to the surface. Coatings could impart these features to the medical devices. In a further example, coating such devices with an antimicrobial surface, may reduce infections associated with microbes, and would be advantageous.

A wide variety of methods have been developed to coat device surfaces to provide them with the desired characteristics. However, the need still exists for a simple, efficient process that will provide stable coatings.

DETAILED DESCRIPTION OF THE INVENTION AND PREFERRED EMBODIMENTS

The present invention provides a simple, economical process for producing devices with stable surface antimicrobial peptide coatings. By "antimicrobial" what is meant is that bacterial adherence to the device surface is reduced in comparison to the uncoated surface, by about 30 percent or more. By "bioactive" what is meant is that the surface provides a beneficial property to the surrounding environment during use. Suitable bioactives, in particular for contact lenses, include peptides, peptides that are, but not limited to hydrophilic peptides, antimicrobial peptides, cationic peptides, anionic peptides, and the like.

The invention provides a method for manufacturing biomedical devices comprising, consisting essentially of, and consisting of curing a reactive monomer mix comprising at least one latent carboxylic acid reactive component, curing said reactive monomer mix to form an article and reacting said article with an antimicrobial peptide coating composition comprising nucleophilic moieties under coating conditions to form a coated article. In another embodiment, the invention provides biomedical devices comprising, consisting essentially of, and consisting of a peptide-coated biomedical device.

By "biomedical device" what is meant is any device designed to be used while in or on either or both human tissue or fluid. Examples of such devices include, without limitation, stents, implants, catheters, and ophthalmic lenses. In a preferred embodiment, the biomedical device is an ophthalmic lens including, without limitation, contact or intraocular lenses. More preferably, the device is a contact lens.

It is an unexpected discovery of the invention that a carboxylate functionality may be readily incorporated into a variety of polymeric articles and subsequently reacted with nucleophilic moieties in peptides and the like coating compositions. The method of the present invention provides a convenient way to covalently bond a variety of peptide coatings to formed polymeric articles. The peptide coatings of the present invention are stable, as well as providing the desired property enhancements. By "stable" is meant that subjecting the coating to autoclaving, washing with a cleaning agent, and/or rinsing with a saline solution does not substantially alter the chemical properties of the biomedical device or coating.

Latent reactive components useful in the invention include, without limitation, ester compounds of the formula R—CO-L wherein R comprises a group capable of cationic, anionic or free radical polymerization and L is a leaving group. Suitable R groups include monovalent groups that can undergo free radical and/or cationic polymerization comprising up to 20 carbon atoms. Preferred R groups comprise free radical reactive groups, such as acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, $C_{2-12}$alkenylphenyls, $C_{2-12}$alkenylnaphthyls, or $C_{2-6}$alkenylphenyl$C_{1-6}$alkyls or a cationic reactive group such as vinyl ethers or epoxide groups and mixtures thereof. Particularly preferred R groups include methacrylates, acryloxys, methacrylamides, acrylamides, and mixtures thereof.

Suitable L groups are stable under reaction conditions, and protect the carboxylate group and leave readily under coating conditions. Suitable L groups include alkyl esters, phenyl esters, hydroxy para-nitroaryls p-nitrophenyl esters, N-hydroxylamine derivatives, and tosylate esters all of which may be substituted or unsubstituted. Preferred L groups include t-butyl esters, 2,4,5-trichlorophenyl esters, pentafluorophenyl esters, N-hydroxysuccinimide esters, N-hydroxy-oxo-dihydrobenzotriazine derivatives, 1-hydroxybenzotriazole esters, tosylate esters, and combinations thereof. Preferred suitable L groups include pentafluorophenyl esters, tosylate esters, and N-hydroxysuccinimide esters, and mixtures thereof. Preferred latent reactive compounds include pentafluoromethacrylate and N-acryloxysuccinimide and mixtures thereof and the like.

The latent reactive component is included in the monomer mix in a coating effective amount. Any amount sufficient to provide the desired level of bonding sites for the coating polymer is sufficient. Suitable amounts include between about 0.01 and 10 weight %, preferably between about 0.01 and 5 weight %, and more preferably between about 0.01 and 1 weight %, all based upon the total weight of the reactive components.

The latent reactive component may be added to any lens material, but is particularly useful for lens materials which do not contain carboxylic acid groups. Suitable lens materials include silicone hydrogels. The reactive components which are useful for making silicone hydrogels are known and comprise silicone containing components, hydrophilic components and optionally, fluorine containing components. Suitable silicone containing components include silicone containing monomers, prepolymers, and macromers. Suitable fluorine containing components include fluorine containing monomers, prepolymers, and macromers.

Suitable siloxane containing monomers include 3-methacryloxy-2-hydroxypropyloxy)propyltris(trimethylsiloxy) silane (SiGMA), 3-methacryloxypropyltris(trimethylsiloxy) silane (TRIS), amide analogs of TRIS described in U.S. Pat. No. 4,711,943, vinylcarbamate or carbonate analogs decribed in U.S. Pat. No. 5,070,215, and monomers contained in U.S. Pat. No. 6,020,445 which are hereby incorporated by reference. More specifically, 3-methacryloxypropyltris(trimethylsiloxy)silane (TRIS), monomethacryloxypropyl terminated polydimethylsiloxanes, polydimethylsiloxanes, 3-methacryloxypropylbis(trimethylsiloxy)methylsilane, methacryloxypropylpentamethyl disiloxane, and combinations thereof are particularly useful as siloxane containing monomers.

Suitable siloxane containing macromers have a number average molecular weight between about 5,000 and about 15,000 Daltons. Siloxane containing macromers include materials comprising at least one siloxane group, and preferably at least one dialkyl siloxane group, and more preferably at least one dimethyl siloxane group. The siloxane containing macromers may include other components such as urethane groups, alkylene or alkylene oxide groups, polyoxyalkalene groups, arylene groups, alkyl esters, amide groups, carbamate groups, perfluoroalkoxy groups, isocyanate groups, combinations thereof and the like. A preferred class of siloxane containing macromers may be formed via the polymerization of one or more siloxanes with one or more acrylic or methacrylic materials. Siloxane containing macromers may be formed via group transfer polymerization ("GTP"), free radical polymerization, condensation reactions, and the like. The siloxane containing macromers may be formed in one or a series of steps depending on the components selected and using conditions known in the art. Specific siloxane containing macromers, and methods for their manufucture, include those disclosed in U.S. Pat. No. 5,760,100 as materials A-D (methacrylate functionalized, silicone-fluoroether urethanes and methacrylate functionalized, silicone urethanes), and those disclosed in U.S. Pat. No. 6,367,929 (styrene functionalized prepolymers of hydroxyl functional methacrylates and silicone methacrylates), the disclosures of which are incorporated herein by reference.

Suitable siloxane containing reactive prepolymers include vinyl carbamate functionalized polydimethylsiloxane, which is further disclosed in U.S. Pat. No. 5,070,215 and urethane based prepolymers comprising alternating "hard" segments formed from the reaction of short chained diols and diisocyantes and "soft" segments formed from a relatively high molecular weight polymer, which is $\alpha,\omega$ end-capped with two active hydrogens. Specific examples of suitable siloxane containing prepolymers, and methods for their manufacture, are disclosed in U.S. Pat. No. 5,034,461, which is incorporated herein by reference.

Generally, the siloxane containing component is present in amounts between about 5 and about 50 weight %, preferably between about 10 and about 50 weight %, and more preferably between about 15 and about 45 weight %, all based upon the total weight of the reactive components.

Suitable fluorine containing monomers include fluorine-containing (meth)acrylates, and more specifically include, for example, fluorine-containing $C_2$-$C_{12}$ alkyl esters of (meth)acrylic acid such as 2,2,2-trifluoroethyl (meth)acrylate, 2,2,2',2',2'-hexafluoroisopropyl (meth)acrylate, 2,2,3,3,4,4,4-heptafluorobutyl (meth)acrylate, 2,2,3,3,4,4,5,5,6,6,7,7,8,8,8-pentadecafluorooctyl (meth)acrylate, 2,2,3,3,4,4,5,5,6,6,7,7,8,8,9,9-hexadecafluorononyl (meth)acrylate and the like. Fluorine containing macromers and reactive prepolymers include macromers and prepolymers which include said fluorine containing monomers. Fluorine containing components may be present in amounts from about 0 to about 10 weight %.

The reactive components of the present invention may also include any hydrophilic monomers used to prepare conventional hydrogels. For example monomers containing acrylic groups ($CH_2$=CRCOX, where R is hydrogen or $C_{1-6}$alkyl an X is 0 or N) or vinyl groups (—C=$CH_2$) may be used. Examples of additional hydrophilic monomers are N,N-dimethylacrylamide, 2-hydroxyethyl methacrylate, glycerol monomethacrylate, 2-hydroxyethyl methacrylamide, polyethyleneglycol monomethacrylate, methacrylic acid, acrylic acid, N-vinyl pyrrolidone, N-vinyl-N-methyl acetamide, N-vinyl-N-ethyl acetamide, N-vinyl-N-ethyl formamide, N-vinyl formamide and combinations thereof.

Aside from the hydrophilic monomers mentioned above, polyoxyethylene polyols having one or more of the terminal hydroxyl groups replaced with a functional group containing a polymerizable double bond may be used. Examples include polyethylene glycol, as disclosed in U.S. Pat. No. 5,484,863, ethoxylated alkyl glucoside, as disclosed in U.S. Pat. No. 5,690,953, U.S. Pat. No. 5,304,584, and ethoxylated bisphenol A, as disclosed in U.S. Pat. No. 5,565,539, reacted with one or more molar equivalents of an end-capping group such as isocyanatoethyl methacrylate, methacrylic anhydride, methacryloyl chloride, vinylbenzoyl chloride, and the like, produce a polyethylene polyol having one or more terminal polymerizable olefinic groups bonded to the polyethylene polyol through linking moieties such as carbamate, urea or ester groups.

Still further examples include the hydrophilic vinyl carbonate or vinyl carbamate monomers disclosed in U.S. Pat. No. 5,070,215, the hydrophilic oxazolone monomers disclosed in U.S. Pat. No. 4,910,277, and polydextran.

The preferred additional hydrophilic monomers are N,N-dimethylacrylamide (DMA), 2-hydroxyethyl methacrylate (HEMA), glycerol methacrylate, 2-hydroxyethyl methacrylamide, N-vinylpyrrolidone (NVP), polyethyleneglycol monomethacrylate, and combinations thereof, with hydrophilic monomers comprising DMA being particularly preferred. Additional hydrophilic monomers may be present in amounts of about 0 to about 70 weight %, more preferably of about 5 and about 60 weight %, and most preferably of about 10 and about 50 weight %, based upon the total weight of the reactive components.

The reactive components may also comprise additional components such as crosslinkers, photoinitiators, visibility tinting agents, and the like. The reactive components are mixed together in the presence of a diluent to form a reaction mixture. Suitable diluents are disclosed in U.S. Pat. No. 6,020,455.

Additional components or additives, which are generally known in the art may also be included in the reactive monomer mix and/or lens material. Additives include but are not limited to ultra-violet absorbing compounds and monomers, reactive tints, antimicrobial compounds, pigments, photochromic compounds, release agents, combinations thereof and the like.

Suitable lens materials include aquafilcon A, balafilcon A, lotrafilcon A, and the like.

Various processes are known for molding the reaction mixture in the production of contact lenses, including spin-casting and static casting. Spincasting methods are disclosed in U.S. Pat. Nos. 3,408,429 and 3,660,545, and static casting methods are disclosed in U.S. Pat. Nos. 4,113,224 and 4,197,266. The preferred method for producing contact lenses comprising the polymer of this invention is by the direct molding of the silicone hydrogel, which is economical, and enables precise control over the final shape of the hydrated lens. For this method, the reaction mixture is placed in a mold having the shape of the final desired silicone hydrogel, i.e. water-swollen polymer, and the reaction mixture is subjected to conditions whereby the monomers polymerize, to thereby produce a polymer in the approximate shape of the final desired product. Then, this polymer mixture is optionally treated with a solvent and then water, producing a silicone hydrogel having a final size and shape which are quite similar to the size and shape of the original molded polymer article. This method can be used to form contact lenses and is further described in U.S. Pat. Nos. 4,495,313; 4,680,336; 4,889,664; and 5,039,459, incorporated herein by reference.

After the biomedical device has been formed, it is reacted with a peptide containing coating. Any peptide compound, which is capable of reacting with a carboxylate to form an ester or an amide, may be used for the coating. Suitable peptide containing coatings contain one or more nucleophilic moieties such as alcohols, primary and secondary amines, and thiol functionalities. These peptide containing coatings include peptides that contain these functionalities, mixtures thereof and the like. Suitable peptides include natural and synthetic peptides comprising amine, alcohol and/or thiol functionalities. In the broadest embodiment of the present invention the sequence of the selected peptide is not critical, so long as the peptide includes one or more of the above listed functionalities which enable attachment according to the process of the present invention. Examples of suitable natural cationic peptides include defensins, magainins, and colicins, with specific examples including protamine, melittin, Cecropin A and nisin. Protamine is isolatable from the sperm of a variety of animals including, without limitation, man. Melittin is isolatable from bee venom. Cecropin A and nisin are isolatable from *Aedes aegypti* and *Lactoccucus lactis*, respectively. Protamine, melittin, cecropin A, and nisin useful in the invention are all commercially available. These cationic peptides and proteins may also be produced by known means. For purposes of the invention, generally the purity of the cationic peptide used is at least about 75%, preferably at least about 90%.

Alternatively, synthetic peptides and proteins may be used. Specific examples include synthetic peptides comprising the 1-26 segment of mellitin, segment A:
  SEQ ID NO: 1 and the 1-17 segment of protamine, segment B:
  SEQ ID NO: 2 present anywhere in a peptide. The peptides may further comprise a third segment C, which may be any linking group which does not inhibit the activity of the peptide or induce toxicity in mammalian cells, and which includes spacers of 0 to about 10 amino acids. Amino acids, as defined herein, refer to any structure with the chemical formula —HN—$(CR^1R^2)_n$—CO—wherein n is an integer between 1 and 21, $R^1$ and $R^2$ are independently selected from the group consisting of H, straight or branched alkyl groups having 1 to 4 carbon atoms, straight or branched hydroxy groups having 1-2 carbon atoms, straight or branched alkylthio groups having 1 to 3 carbon atoms, carbamoyl groups having 1 to 3 carbon atoms, carboxy groups having 1 to 3 carbon atoms, primary and secondary amino groups having 1 to 4 carbon atoms and 1 to 3 nitrogen atoms, benzyl, phenol, phenyl indoles and N,N-pyrroles. Preferably n is an integer between 1 and 10 and at least one of $R^1$ and $R^2$ is H and the other is selected from the above. The A, B and C segments of the synthetic peptide may be in any order and may be repeated in part or whole. In a preferred embodiment, the A and B segments are in terminal positions and in another preferred embodiment the synthetic peptide has the formula ACB or BCA and C comprises up to 5 amino acids.

The invention also includes peptides that are conservative variations of those peptides exemplified herein. The term "conservative variation" as used herein denotes a polypeptide in which at least one amino acid is replaced by another, biologically similar residue. Examples of conservative variations include the substitution of one hydrophobic residue, such as isoleucine, valine, leucine, alanine, cysteine, glycine, phenylalanine, proline, tryptophan, tyrosine, norleucine or methionine for another, or the substitutions of one polar residue for another such as the substitution of arginine for lysine, glutamic acid for aspartic acid or glutamine for asparagine and the like. Neutral hydrophilic amino acids that can be substituted for one another include asparagine, glutamine, serine and threonine.

The term "peptide", as used herein, refers to the basic chemical structure of polypeptides that is well known and has been described in textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types. It will be appreciated that polypeptides often contain amino acids other than the 20 amino acids commonly referred to as the 20 naturally occurring amino acids, and that many amino acids, including the terminal amino acids, can be modified in a given polypeptide, either by natural processes, such as processing and other post-translational modifications, and also by chemical modification techniques which are well known to the art. Even the common modifications that occur naturally in polypeptides are too numerous to list exhaustively here, but they are well described in basic texts and in more detailed monographs, as well as in a voluminous research literature, and they are well known to those of skill in the art. Among the known modifications which can be present in polypeptides of the present are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York (1993). Many detailed reviews are available on this subject, such as, for example, those provided by Wold, F., Posttranslational Protein Modifications: Perspectives and Prospects, pgs. 1-12 in POST-TRANSLATIONAL COVALENT MODIFICATION OF PROTEINS, B. C. Johnson, Ed., Academic Press, New York (1983); Seifter et al., (1990), *Meth. Enzymol.* 182, 626-646 and Rattan et al., "Protein Synthesis: Posttranslational Modifications and Aging", (1992) Ann. N.Y. Acad. Sci. 663, 48-62. It will be appreciated, as is well known and as noted above, that polypeptides are not always entirely linear. For instance, polypeptides (both linear and non-linear) can be generated as a result of posttranslational events, including natural processing events and events brought about by human manipulation which do not occur naturally. Circular, branched and branched circular polypeptides can be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications can be present in polypeptides of the present invention, as well. For instance, the amino terminal residue of polypeptides made in *E. coli* or other cells, prior to proteolytic processing, almost invariably will be N-formyl-methionine. During post-translational modification of the peptide, a methionine residue at the $NH_2$-terminus can be deleted. Accordingly, this invention contemplates the use of both the methionine-containing and the methionineless amino terminal variants of the protein of the invention. The modifications that occur in a polypeptide often will be a function of how it is made. For polypeptides made by expressing a cloned gene in a host, for instance, the nature and extent of the modifications in large part will be determined by the host cell posttranslational modification capacity and the modification signals present in the polypeptide amino acid sequence. For instance, as is well known, glycosylation often does not occur in bacterial hosts such as, for example, *E. coli*. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having native patterns of glycosylation, inter alia. Similar considerations apply to other modifications. It will be appreciated that the same type of modification can be present in the same or varying degree at several sites in a given polypeptide. Also, a given polypeptide can contain many types of modifications. In general, as used herein, the term polypeptide encompasses all such modifications, particularly those that are present in polypeptides synthesized recombinantly by expressing a polynucleotide in a host cell.

As used herein "Melimine" refers to a polypeptide comprising an amino acid sequence of:
SEQ ID NO: 3

Wherein: T is threonine, L is leucine, I is isoleucine, S is serine, W is tryptophan, K is lysine, N is asparagine, R is arginine, Q is glutamine, P is Proline, V is valine, G is glycine. As used herein, L-melimine comprises the above amino acid sequence as it exists naturally. Optical isomers of amino acids undergo spontaneous nonenzymatic racemisation. This rate varies for each amino acid at a given temperature or pH (storage conditions), but is more rapid in D than L isomers. As used herein L- or D-peptides will comprise about 99% L or D isomers, respectively at a pH of 7 and a temperature of about 250 °C.

L-amino acids are the naturally occurring form in biological systems, therefore D-isomers are more resistant to enzymatic breakdown and may have an increased persistance. This property may be exploited by the use of mixtures of the stereoisomers to give desired levels of activity and longevity for a particular application. So, for applications where long term persistence is desired, the use of a stereoisomeric mixture having a predominance (greater than about 50% and preferably greater than about 70%) D isomer may be preferred. Where greater antibacterial activity is desired the use of a stereoisomeric mixture having a predominance (greater than about 50% and preferably greater than about 70%) L isomer may be preferred.

As used herein "Protattin" refers to a polypeptide comprising an amino acid sequence of
SEQ ID NO: 4

Wherein the amino acids are as defined above.

For purposes of the invention, generally the cationic peptide used is substantially purified.

As used herein, the term "substantially purified" means that the protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals that are involved in the synthesis of the protein. Accordingly such preparations of the protein have less than about 30%, 20%, 10%, 5% (by dry weight) of chemical precursors or compounds other than the polypeptide of interest.

Peptides of the invention can be synthesized chemically using standard peptide synthesis techniques. Alternatively, a peptide of the invention can be synthesized in an in vitro translation and/or transcription system.

Polypeptides may be synthesized using conventional solid-phase peptide synthesis protocols. Such methods are well known to those skilled in the art. What follows is a descriptive way of making a polypetide using the solid phase synthetic technique, but in no way limits the scope of this invention to this method. The synthesis is performed on any suitable synthesis resin. Suitable resins include insoluble cross-linked polystyrene resin and the like. The amino acids are generally protected using fluorenylmethoxycarbonyl groups and the like and activated with N-hydroxybenzotriazole and, optionally, diisopropylcarbodiimide (DIC) to facilitate their coupling. The completed peptide is cleaved from the resin using, but not limited to trifluoroacetic acid or ammonia and the resulting material purified by reverse-phase high-performance liquid chromatography (HPLC), after which the candidate material was freeze-dried from a water/acetonitrile mixture to a dry powder.

Polypeptides of the invention can also be produced using an in vitro translation and/or transcription system. Such methods are known to those skilled in the art. For example, synthetic mRNA encoding a Melimine or Protattin can be efficiently translated in various cell-free systems, including but not limited to wheat germ extracts and reticulocyte extracts. Alternatively, synthetic DNA comprising the coding sequence for a Melimine or Protattin under the control of a T7 promoter can be efficiently transcribed and translated, in an in vitro transcription and translation system, such as the TNT T7 coupled Reticulocyte Lysate System, which is commercially available from Promega. The resulting polypeptide can be purified by method described herein. Preferred peptide containing coating polymers include melimine, protattin and combinations thereof.

In the process of the invention, the surface to be coated is contacted with the coating peptide in any convenient manner. For example, the device may be placed in a solution of coating peptide and solvent and coupling additives.

Suitable solvents for use in the invention are non-nucleophilic solvents capable of solubilizing the coating peptide without negatively reacting with the biomedical device. Suitable solvents include, but are not limited to, DMF, DMSO, ethyl acetate, DPMA, mixtures thereof and the like. Preferred solvents include DMF and DPMA.

The device is contacted with the solvent/coating peptide solution under conditions suitable to form the coating. Suitable temperatures include those between the freezing and boiling points of the selected solvent, preferably between about 0 and about 100° C. and more preferably between about 20 and about 50° C. The contact time used will be a length of time sufficient to coat the surface to the extent desired. Contact times may be up to about 2 days, preferably up to about 1 day, and most preferably up to about 12 hours. Pressure is not critical in the coating reaction of the present invention. However, those of skill in the art will recognize that elevated pressures and temperatures will enable the reaction to be conducted in a shorter period of time.

Coupling additives are any compound(s) that enables the amide and/or ester linkage between the device(s) and peptide coating(s) to be formed more readily than without their addition and include, but are not limited to, trans-esterification reagents, catalysts, thereof and the like. Examples include 4-dimethylaminopyridine (DMAP), 1-(3-dimethylaminopropyl)-3-ethylcarbodiimide hydrochloride salt (EDC), 1,3-diisopropylcarbodiimide, 1,3-dicyclohexylcarbodiimide, 1-hydroxybenzotriazole (HOBt), 1-hydroxybenzotriazole hydrate, crown ethers, acids, bases, enzymes, combinations thereof and the like.

A coating effective amount of coating peptide is used, meaning an amount sufficient to coat the surface to the desired degree. Generally, the amount of coating peptide used is about 0.1 to about 20 weight %, preferably about 0.5 to about 10 weight %, and more preferably, about 0.8 to about 5 weight % of the coating solution.

Following contacting, the surface may be washed with water or buffered saline solution to remove unrelated (or unreacted) peptide, leaving group, solvent, and byproducts. Optionally, the peptide coated surface may be heated in water to extract residual peptide, leaving group, and byproducts and to ensure the break down of leaving group complexes that may have formed.

The invention will be further clarified by a consideration of the following, non-limiting examples. The following tests were used in the examples.

Lenses were analyzed for their coatings using the FTIR-ATR line scan technique using a Perkin-Elmer Spectrum GX FTIR AutoIMAGE System. All line scans were made with 300-micron incremental steps from edge to edge in the center region of the lens. All samples were analyzed in wet state.

The advancing contact angle was measured as follows. At least three samples from each set were prepared by cutting out a center strip from the lens approximately 5 mm in width and equilibrated in packing solution. The wetting force between the lens surface and borate buffered saline is measured at 23° C. using a Wilhelmy microbalance while the sample is being immersed into or pulled out of the saline. The following equation is used $$F = 2\gamma p \cos \theta$$

or $$\theta = \cos^{-1}(F/2\gamma p)$$

where F is the wetting force, $\gamma$ is the surface tension of the probe liquid, p is the perimeter of the sample at the meniscus and 0 is the contact angle. The advancing contact angle is obtained from the portion of the wetting experiment where the sample is being immersed into the packing solution. Each sample was cycled four times and the results were averaged to obtain the advancing contact angles for the lens.

Haze is measured by placing a hydrated test lens in borate buffered saline in a clear 20×40×10 mm glass cell at ambient temperature above a flat black background, illuminating from below with a fiber optic lamp (Titna Tool Supply Co. fiber optic light with 0.5" diameter light guide set at a power setting of 4-5.4) at an angle 66° normal to the lens cell, and capturing an image of the lens from above, normal to the lens cell with a video camera (DVC 1300C:19130 RGB camera with Navitar TV Zoom 7000 zoom lens) placed 14 mm above the lens platform. The background scatter is subtracted from the scatter of the lens by subtracting an image of a blank cell using EPIX XCAP V 1.0 software. The subtracted scattered light image is quantitatively analyzed, by integrating over the central 10 mm of the lens, and then comparing to a −1.00 diopter CSI Thin Lens®, which is arbitrarily set at a haze value of 100, with no lens set as a haze value of 0. Five lenses are analyzed and the results are averaged to generate a haze value as a percentage of the standard CSI lens.

The water content was measured as follows: lenses to be tested are allowed to sit in packing solution for 24 hours. Each of three test lens are removed from packing solution using a sponge tipped swab and placed on blotting wipes which have been dampened with packing solution. Both sides of the lens are contacted with the wipe. Using tweezers, the test lens are placed in a weighing pan and weighed. Two more sets of samples are prepared and weighed as above. The pan is weighed three times and the average is the wet weight.

The dry weight is measured by placing the sample pans in a vacuum oven which has been preheated to 60° C. for 30 minutes. Vacuum is applied until at least 0.4 inches Hg is attained. The vacuum valve and pump are turned off and the lenses are dried for four hours. The purge valve is opened and the oven is allowed reach atmospheric pressure. The pans are removed and weighed. The water content is calculated as follows:

Wet weight = combined wet weight of pan and lenses −
weight of weighing pan

Dry weight = combined dry weight of pan and lens −
weight of weighing pan $$\% \text{ water content} = \frac{(\text{wet weight} - \text{dry weight})}{\text{wet weight}} \times 100$$

The average and standard deviation of the water content are calculated for the samples are reported.

Modulus is measured by using the crosshead of a constant rate of movement type tensile testing machine equipped with a load cell that is lowered to the initial gauge height. A suitable testing machine includes an Instron model 1122. A dog-bone shaped sample having a 0.522 inch length, 0.276 inch "ear" width and 0.213 inch "neck" width is loaded into the grips and elongated at a constant rate of strain of 2 in/min. until it breaks. The initial gauge length of the sample (Lo) and sample length at break (Lf) are measured. Twelve specimens of each composition are measured and the average is reported. Tensile modulus is measured at the initial linear portion of the stress/strain curve.

In the following examples the bound peptide was quantified by a method developed by Cole and Ralston (1994). Contact lenses were stained for 2-24 hours using filtered 0.025% Coomassie stain in 10% acetic acid and 10% iso-propanol at 37° C. Lenses were destained in 10% acetic acid and 10% iso-propanol at 37° C. Lenses were then extracted in 25% Pyridine overnight. The extracted solutions were analysed in the spectrophotometer at A600 using 25% Pyridine as a blank. L-Melimine quantification was determined by correlating extracts against a standard curve constructed by pipetting known amounts of L-Melimine on semi-dried acrylamide gels and extracting as above, this method extracts all amounts of peptide from the gel.

EXAMPLES

Example 1

To a dry container housed in a dry box under nitrogen at ambient temperature was added 30.0 g (0.277 mol) of bis(dimethylamino)methylsilane, a solution of 13.75 ml of a 1M solution of TBACB (386.0 g TBACB in 1000 ml dry THF), 61.39 g (0.578 mol) of p-xylene, 154.28 g (1.541 mol) methyl methacrylate (1.4 equivalents relative to initiator), 1892.13 (9.352 mol) 2-(trimethylsiloxy)ethyl methacrylate (8.5 equivalents relative to initiator) and 4399.78 g (61.01 mol) of THF. To a dry, three-necked, round-bottomed flask equipped with a thermocouple and condenser, all connected to a nitrogen source, was charged the above mixture prepared in the dry box.

The reaction mixture was cooled to 15° C. while stirring and purging with nitrogen. After the solution reaches 15° C., 191.75 g (1.100 mol) of 1-trimethylsiloxy-1-methoxy-2-methylpropene (1 equivalent) was injected into the reaction vessel. The reaction was allowed to exotherm to approximately 62° C. and then 30 ml of a 0.40 M solution of 154.4 g TBACB in 11 ml of dry THF was metered in throughout the remainder of the reaction. After the temperature of reaction reached 30° C. and the metering began, a solution of 467.56 g (2.311 mol) 2-(trimethylsiloxy)ethyl methacrylate (2.1 equivalents relative to the initiator), 3636.6. g (3.463 mol) n-butyl monomethacryloxypropyl-polydimethylsiloxane (3.2 equivalents relative to the initiator), 3673.84 g (8.689 mol) TRIS (7.9 equivalents relative to the initiator) and 20.0 g bis(dimethylamino)methylsilane was added.

The mixture was allowed to exotherm to approximately 38-42° C. and then allowed to cool to 30° C. At that time, a solution of 10.0 g (0.076 mol) bis(dimethylamino)methylsilane, 154.26 g (1.541 mol) methyl methacrylate (1.4 equivalents relative to the initiator) and 1892.13 g (9.352 mol) 2-trimethylsiloxy)ethyl methacrylate (8.5 equivalents relative to the initiator) was added and the mixture again allowed to exotherm to approximately 40° C. The reaction temperature dropped to approximately 30° C. and 2 gallons of THF were added to decrease the viscosity. A solution of 439.69 g water, 740.6 g methanol and 8.8 g (0.068 mol) dichloroacetic acid was added and the mixture refluxed for 4.5 hours to de-block the protecting groups on the HEMA. Volatiles were then removed and toluene added to aid in removal of the water until a vapor temperature of 110° C. was reached.

The reaction flask was maintained at approximately 110° C. and a solution of 443 g (2.201 mol) TMI and 5.7 g (0.010 mol) dibutyltin dilaurate were added. The mixture was reacted until the isocyanate peak was gone by IR. The toluene was evaporated under reduced pressure to yield an off-white, anhydrous, waxy reactive monomer. The macromer was placed into acetone at a weight basis of approximately 2:1 acetone to macromer. After 24 hrs, water was added to precipitate out the macromer and the macromer was filtered and dried using a vacuum oven between 45 and 60° C. for 20-30 hrs.

Examples 2

A reaction mixture was formed by adding 100 parts of the components shown in Table 1, in the amounts shown in Table 1 with 20 parts 3,7-dimethyl-3-octanol. Specifically, in the following order macromer, Norbloc 7966, diluent, TEGDMA, HEMA, DMA, TRIS, and mPDMS were added to an amber flask. These components were mixed at 170-300 rpm, at 50-55° C., for 90 to 180 minutes. While maintaining mixing, blue HEMA was added and the components mixed for a further 20 to 75 minutes (at 170-300 rpm, 50-55° C.). Still with mixing, PVP was added and the mixture stirred for another 20 to 140 minutes (at 170-300 rpm, 50-55° C.). Lastly, with continual mixing, CGI 1850 (Irgacure 1850) was added.

TABLE 1

| Component | Weight Percent |
| --- | --- |
| Macromer (Ex 1) | 18.95 |
| TRIS | 14.74 |
| DMA | 27.37 |
| MPDMS | 29.47 |
| NORBLOC | 2.11 |
| CGI 1850 | 1.05 |
| TEGDMA | 1.05 |
| HEMA | 5.26 |

Pentafluorophenyl methacrylate (OPfp) (0.5 wt %) was added to the reaction mixture. The reaction mixture was mixed vigorously for approximately 10 minutes (or until the solution appeared clear and evenly mixed) and the then degassed, on high vacuum, until no air bubbles were visible in the reaction mixture (about 20 minutes). The reaction mixtures were placed into thermoplastic contact lens molds, and irradiated using Philips TL 20W/03T fluorescent bulbs at 50° C., for about 50 minutes in an $N_2$ atmosphere. The lenses were demolded in Dowanol® DPMA (DPMA, commercially available from Aldrich). Lenses were washed up to five times with DPMA. Each wash lasted about 120 minutes. The lenses were individually placed into vials containing 2 mL of a solution with 2.5 mg/mL melimine and 0.05 weight percent of N,N'-diisopropylethylamine (DIPEA) in dimethylformamide (DMF). The vials (containing the lenses and solution) were stoppered with gray butyl stoppers and then incubated in an Incubator Shaker for 18-hours at 37° C., shaking continuously at 100 rpm.

After incubation the solvent from each of the vials was removed. Approximately 9 mL of fresh DMF solvent was then added to each vial. After 1-hour the solvent was removed and fresh DMF solvent was re-added at the same volume. This process was repeated a total of 4-times each at 1-hour intervals. After the fourth solvent change out the lenses were placed directly into DI water at room temperature and washed 4-times at 1-hour intervals. After the fourth wash the lenses were placed into packing solution at room temperature for 1-hour and then autoclaved for 30-minutes at 121° C. Lens properties were measured and are shown in Table 2, below.

Example 3

Example 2 was repeated except that coupling additives were added to the melimine-containing coating solution. So, exactly as per Example 2 and the lenses after being release and washed in DPMA solvent, were placed into individually into vials containing 3 mL of a solution of 5 mg/mL of N-hydroxybenzotriazole (HOBt) in DMF. Using a calibrated pipettor, 50 μL of diisopropylcarbodiimide (DIC) was added to each vial. After 20 minutes, 1 mL of a 3 mg/mL melimine in DMF solution containing 0.05 weight percent of N,N'-diisopropylethylamine (DIPEA) was added to each vial using a calibrated Eppendorf pipettor. The vials were stoppered with gray butyl stoppers. The lenses were then incubated in an Incubator Shaker for 19-hours at 37° C. with shaking continuously at 100 rpm.

After incubation the solvent from each of the vials was removed. Approximately 9 mL of fresh DMF solvent was then added to each vial. After 1-hour the solvent was removed and fresh DMF solvent was re-added at the same volume. This process was repeated a total of 4-times each at 1-hour intervals. After the fourth solvent change out the lenses were placed directly into DI water at room temperature and washed 4-times at 1-hour intervals. After the fourth wash the lenses were placed into packing solution at room temperature for 1-hour and then autoclaved for 30-minutes at 121° C. Lens properties were measured and are shown in Table 2, below.

TABLE 2

| Property | Control 1 | Ex 2 | Ex 3 |
| --- | --- | --- | --- |
| Water Content (%) | 35.1 (0.2) | 35.6 (0.3) | 35.4 (0.2) |
| Modulus (psi) | 113.0 (11.9) | 119.9 (10.3) | 132.9 (13.0) |
| Elongation (%) | 176.5 (75.1) | 128.2 (67.8) | 213.1 (56.6) |
| Tensile Strength (psi) | 93.1 (45.8) | 72.4 (43.6) | 127.2 (35.5) |
| Toughness (psi) | 91.7 (60.0) | 53.5 (59.0) | 131.0 (62.2) |
| DCA (°) | 96 (20) | 95 (13) | 67 (25) |

TABLE 2-continued

| Property | Control 1 | Ex 2 | Ex 3 |
| --- | --- | --- | --- |
| Melimine Concentration (ug/lens) | N/A | ≈120 | ≈140 |

Examples 4-7

Example 3 was repeated except that the concentrations of the melimine-coating solution and the wash procedure were changed. So, exactly as per Example 3, the lenses after being released and washed in DPMA solvent, were placed into individually into vials containing 3 mL of a solution of 5 mg/mL of N-hydroxybenzotriazole (HOBt) in DMF. Using a calibrated pipettor, 50 μL of diisopropylcarbodiimide (DIC) was added to each vial. After about 60 minutes at room temperature, 1 mL of a melimine-coating solution of various concentration listed in Table 3, in DMF containing 0.05 weight percent of N,N-diisopropylethylamine (DIPEA) was added to each vial using a calibrated Eppendorf pipettor. The vials were stoppered with gray butyl stoppers. The lenses were then incubated in an Incubator/Shaker for about 19 hours at 37° C. with shaking continuously at 100 rpm.

After incubation, lenses were transferred to a 400 mL beaker containing 300 mL of fresh DMF and a magnetic stirrer. The lenses were stirred in the DMF for 1 hour. This process was repeated three more times (four times total). After the fourth solvent change out, the 300 mL of DI water was added to the beaker and the lenses washed a total of four times with DI water. After the fourth wash, the lenses were placed into vials containing packing solution and then autoclaved for 30 minutes at 121° C. Lens properties were measured and are shown in Table 3, below. Standard deviations are shown in parenthesis.

TABLE 3

| Property | Control 2 | Ex 4 | Ex 5 | Ex 6 | Ex 7 |
| --- | --- | --- | --- | --- | --- |
| Coating Solution Conc. (mg/mL) | 0 | 0.75 | 1.50 | 3.00 | 6.00 |
| Water Content (%) | 35.8 (0.3) | N/M | 35.5 (0.3) | 35.6 (0.3) | N/M |
| Modulus (psi) | 95 (8) | N/M | 111 (13) | 107 (8) | 108 (12) |
| Elongation (%) | 134 (70) | N/M | 164 (82) | 161 (66) | 155 (55) |
| Tensile Strength (psi) | 55 (28) | N/M | 80 (43) | 77 (34) | 72 (25) |
| Toughness (psi) | 44 (42) | N/M | 77 (67) | 68 (53) | 59 (39) |
| DCA (°) | N/M | N/M | N/M | N/M | N/M |
| Melimine Conc. (ug/lens) | | 63 | 128 | 219 | 334 |

N/M indicates not measured.

What is claimed is:

1. A process for manufacturing coated biomedical devices comprising the step of contacting at least one surface of a biomedical device formed from a silicone hydrogel reactive mixture which does not contain carboxylic acid groups, and at least one latent reactive component with a coating effective amount of at least one peptide containing coating comprising at least one synthetic peptide comprising three segments, A, B and C, wherein A and B are in terminal positions and segment A is a peptide having the sequence:

SEQ ID NO: 1 segment B is a peptide having the sequence:

SEQ ID NO: 2 and segment C is a linking group of up to 10 amino acids, which does not inhibit the antimicrobial activity of the peptide or induce toxicity in mammalian cells.

2. The process of claim 1 wherein the biomedical device is a contact lens.

3. The process of claim 2 wherein said latent reactive component is at least one ester compound of the formula R—CO-L wherein R comprises a group capable of cationic, anionic or free radical polymerization and L is a leaving group.

4. The process of claim 3 wherein said R group is selected from the group consisting of acrylates, styryls, vinyls, vinyl ethers, $C_{1-6}$alkylacrylates, acrylamides, $C_{1-6}$alkylacrylamides, N-vinyllactams, N-vinylamides, $C_{2-12}$alkenyls, C2-12alkenylphenyls, $C_{2-12}$alkenylnaphthyls, $C_{2-6}$alkenylphenyl$C_{1-6}$alkyls, vinyl ethers and epoxide groups.

5. The process of claim 3 wherein said R group is selected from the group consisting of methacrylates and acryloxys.

6. The process of claim 3 wherein said L group are selected from the group consisting of hydroxyalkyls, hydroxyaryls, hydroxy para-nitroaryls, alkyl esters, phenyl esters, p-nitrophenyl esters, N-hydroxylamine derivatives, and tosylates all of which may be substituted or unsubstituted.

7. The process of claim 3 wherein said L group is selected from the group consisting of t-butyl esters, 2,4,5-trichlorophenyl esters, pentafluorophenyl esters, N-hydroxysuccinimide esters, N-hydroxy-oxo-dihydrobenzotriazine derivatives, and 1-hydroxybenzotriazole esters.

8. The process of claim 3 wherein said at least one latent reactive compound comprises pentafluoromethacrylate, N-acryloxysuccinimide and mixtures thereof.

9. The process of claim 3 wherein said latent reactive component is included in the reactive mixture in an amount between about 0.01 and about 10 weight % based upon the total weight of the reactive components.

10. The process of claim 3 wherein said latent reactive component is included in the reactive mixture in an amount between about 0.01 and about 5 weight % based upon the total weight of the reactive components.

11. Theprocess of claim 3 wherein said latent reactive component is included in the reactive mixture in an amount between about 0.01 and about 1 weight %, based upon the total weight of the reactive components.

12. The process of claim 2 wherein said reactive mixture comprises at least one silicone containing component and at least one hydrophilic component.

13. The process of claim 1 wherein segment C has a formula —HN—$(CR^1R^2)_n$—CO— wherein n is an integer between 1 and 21, $R^1$ and $R^2$ are independently selected from the group consisting of H, straight or branched alkyl groups having 1 to 4 carbon atoms, straight or branched hydroxy groups having 1-2 carbon atoms, straight or branched alkylthio groups having 1 to 3 carbon atoms, carbamoyl groups having 1 to 3 carbon atoms, carboxy groups having 1 to 3 carbon atoms, primary and secondary amino groups having 1 to 4 carbon atoms and 1 to 3 nitrogen atoms, benzyl, phenol, phenyl indoles and N,N-pyrroles.

14. The process of claim 13 wherein n is an integer between 1 and 10 and at least one of $R^1$ and $R^2$ is H.

15. The device of claim 1 wherein the A and B segments are in terminal positions and segment C comprises up to 5 amino acids.

16. The process of claim 1 wherein said contacting step comprises placing said device in a solution comprising said coating peptide and solvent.

17. The process of claim 16 wherein said solvent is selected from the group consisting of DMF, DSMO, ethyl acetate, DPMA and mixtures thereof.

18. The process of claim 16 wherein said contacting step comprises a temperature between about 0 and about 100° C.

19. The process of claim 16 wherein said contacting step comprises a temperature between about 20 and about 50° C.

20. The process of claim 16 wherein said contacting step comprises a contact time of up to about 2 days.

21. The process of claim 16 wherein said contacting step comprises a contact time of up to about 12 hours.

22. The process of claim 16 wherein said solution further comprises at least one coupling additive.

23. The process of claim 22 wherein said coupling additive is selected from the group consisting of 4-dimethylaminopyridine (DMAP), 1-(3-dimethylaminopropyl)-3-ethylcarbodiimide hydrochloride salt (EDC), 1,3-diisopropylcarbodiimide, 1,3-dicyclohexylcarbodiimide, 1-hydroxybenzotriazole (HOBt), 1-hydroxybenzotriazole hydrate, crown ethers, acids, bases, enzymes and combinations thereof.

24. A biomedical device formed from a silicone hydrogel reactive mixture which does not contain carboxylic acid groups comprising at least one latent reactive component of the formula R-CO—L wherein R comprises a group capable of cationic, anionic or free radical polymerization and L is a leaving group, wherein said device is coated with a coating effective amount of at least one peptide containing coating wherein said peptide comprises three segments, A, B and C, wherein A and B are in terminal positions and segment A is a peptide having the sequence:

SEQ ID NO: 1 segment B is a peptide having the sequence:

SEQ ID NO: 2 and segment C is a linking group of up to 10 amino acids, which does not inhibit the antimicrobial activity of the peptide or induce toxicity in mammalian cells.

25. The device of claim 24 wherein the biomedical device is a contact lens.

26. The device of claim 24 wherein said reactive mixture comprises at least one silicone containing component and at least one hydrophilic component.

27. The device of claim 24 wherein said coating peptide comprises one or more nucleophilic moiety selected from the group consisting of alcohol, primary amine, secondary amine, thiol and combinations thereof.

28. The process of claim 16 wherein said solvent comprises DMF, DPMA or mixtures thereof.

29. The process of claim 16 wherein said contacting step comprises a temperature between the freezing and boiling points of said solvent.

30. The process of claim 1 wherein said reactive mixture comprises silicone containing components, hydrophilic components, and optionally further comprising fluorine containing components.

* * * * *

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: Synthetic Peptides

<400> SEQUENCE: 1

Thr Leu Ile Ser Trp Ile Lys Asn Lys Arg Lys Gln
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic Peptides

<400> SEQUENCE: 2

Arg Pro Arg Val Ser Arg Arg Arg Arg Arg Arg Gly Gly Arg Arg Arg
1               5                   10                  15

Arg

<210> SEQ ID NO 3
<211> LENGTH: 29
<212> TYPE: PRT
<213> ORGANISM: Artificial Sequence
<220> FEATURE:
<223> OTHER INFORMATION: Synthetic  Peptides

<400> SEQUENCE: 3

Thr Leu Ile Ser Trp Ile Lys Asn Lys Arg Lys Gln Arg Pro Arg Val
1               5                   10                  15

Ser Arg Arg Arg Arg Arg Arg Gly Gly Arg Arg Arg Arg
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic  Peptides

<400> SEQUENCE: 4

Arg Pro Arg Val Ser Arg Arg Arg Arg Arg Arg Gly Gly Arg Arg Arg
1               5                   10                  15

Arg Thr Leu Ile Ser Trp Ile Lys Asn Lys Arg Lys Gln
            20                  25